United States Patent [19]

Berg

[11] Patent Number: 5,557,077
[45] Date of Patent: Sep. 17, 1996

[54] HEARING-PROTECTOR PLUG

[75] Inventor: Bengt G. Berg, Tyringe, Sweden

[73] Assignee: Bilsom AB, Billesholm, Sweden

[21] Appl. No.: 129,034

[22] PCT Filed: Dec. 16, 1993

[86] PCT No.: PCT/SE92/00240

§ 371 Date: Oct. 5, 1993

§ 102(e) Date: Oct. 5, 1993

[87] PCT Pub. No.: WO92/18076

PCT Pub. Date: Oct. 29, 1992

[30] Foreign Application Priority Data

Apr. 19, 1991 [SE] Sweden ............................ 9101181

[51] Int. Cl.⁶ ............................................ A61B 7/02
[52] U.S. Cl. ............................................ 181/135; 128/864
[58] Field of Search ........................... 181/129, 130, 181/135; 128/864–868; 340/568, 572

[56] References Cited

U.S. PATENT DOCUMENTS

| | | | |
|---|---|---|---|
| 3,696,090 | 10/1972 | Lampe | 264/222 |
| 3,782,379 | 1/1974 | Lampe | 264/222 |
| 3,897,376 | 7/1975 | Lampe | 264/222 |
| 4,314,553 | 2/1982 | Westerdal | 128/152 |
| 4,498,469 | 2/1985 | Csiki | 128/152 |
| 4,614,487 | 9/1986 | Csiki | 425/112 |
| 4,936,411 | 6/1990 | Leonard | 181/135 |

FOREIGN PATENT DOCUMENTS

| | | |
|---|---|---|
| 0244979 | 11/1987 | European Pat. Off. . |
| 9001914 | 3/1990 | WIPO . |

OTHER PUBLICATIONS

International Search Report and Annex.
International Preliminary Examination Report.

*Primary Examiner*—Khanh Dang
*Attorney, Agent, or Firm*—Greenblum & Bernstein P.L.C.

[57] ABSTRACT

Hearing-protector plug made of plug material in which there is distributed a detectable material in powder form, particularly iron powder. If lost, such as in the food industry, the plug can be traced with the aid of detection equipment.

15 Claims, No Drawings

HEARING-PROTECTOR PLUG

FIELD OF THE INVENTION

The present invention relates to a hearing-protector plug, in the following referred to as an ear plug, which is designed to be applied in the ear and comprises means that enable it to be detected if lost.

DISCUSSION OF BACKGROUND MATERIAL

In the food industry, in particular, it is important that foreign objects are not lost, thereby possibly ending up in the foodstuff. This also goes for ear plugs.

Previously, efforts have been made to eliminate this inconvenience by interconnecting two ear plugs by a band or a cord. Under unfavourable conditions, however, an ear plug may nevertheless be lost. Further, the entire unit comprising the two ear plugs and the band or string may, of course, be lost as well.

In recent years, ear plugs have therefore been equipped with special means that can be detected with the aid of conventional detection equipment usually operating magnetically or electrically, whereby a lost ear plug can be traced.

EP-A1-0,244,979 discloses the provision of a special metal ferrule in the shank portion of an ear plug, one end of a connecting cord being fixed in the metal ferrule which in turn is mounted by press fit in an axial hole formed in the shank of the plug. If a lost ear plug of this type is to be detected, the metal ferrule has to stay in place in the ear plug. However, this is not always the case, and the metal ferrule may instead stick to the end of the connecting cord. When it does, the lost ear plug, of course, cannot be detected.

U.S. Pat. No. 4,936,411 discloses an ear plug similar to that described in EP-A1-0,244,979. In this case, however, a detectable metal sphere is mounted in the hole formed in the shank of the ear plug, inwardly of the fixing point of the end of the associated connecting cord. This is meant to ensure that the metal sphere will at all times stay with the ear plug if this is lost.

It will, however, be appreciated that a lost ear plug may easily be exposed to such conditions that it comes apart, in particular so that the shank portion of the ear plug detaches itself from the main body thereof. If so, the main body cannot possibly be detected.

OBJECT OF THE INVENTION

The object of the present invention is to provide an improved ear plug of the type stated in the introduction to this specification, thereby obviating the above inconveniences while affording advantages of manufacturing technique and economy, without adversely affecting the other properties of the ear plug.

SUMMARY OF THE INVENTION

The ear plug according to the invention is thus mainly characterized in that the means added to give detectability is finely divided and distributed in the plug material, preferably, homogeneously distributed throughout the plug. The detectable means can thus be in powder form and be an integral part of the plug material.

According to the invention, the detectable means can be simply added to the plug material before the plug is manufactured. As will be appreciated, this involves considerable advantages as to processing technique and costs.

With a homogeneous mixing of the means in the entire plug, also small pieces of a lost plug can be detected, e.g., magnetically or electrically, with the aid of conventional equipment used, e.g., in the food industry.

Distributing the means in the plug material according to the invention has been found to have no negative effects on the function of the ear plug or its wearing comfort.

The detectable means advantageously consists of a metal powder, preferably iron powder. It will, however, be appreciated that any detectable powder material can be used.

Use is advantageously made of iron powder of the type employed in the food and pharmaceutical industries, e.g., in iron tablets. It may thus be a question of water-atomized, sponge-iron-base or electrooxidized iron powders. The powder particles are advantageously surface-treated prior to admixture so as to improve adhesion to the plug material and prevent oxidation.

Conveniently, the particle size of the pulverulent means should not exceed about 300 μm. The particle size is advantageously between about 50 μm and 200 μm, typically about 80 μm.

When the ear plugs are molded, especially of silicone material, the means can be admixed to the plug material prior to molding.

When the ear plugs are made of foamed plastic, the means can be admixed to the plastic material prior to foaming.

When the ear plugs are made of fine glass fibers, so-called glass down, the means can be freely distributed in the down, particularly when the plug has a special outer casing. Also, the means can be applied by finishing technique.

The invention will be described in more detail below with the aid of an Example.

EXAMPLE

For a silicone plug of the type described in our U.S. Pat. No. 4,314,553, where more detailed information on the plug design and so forth can be found, about 40 parts by weight of iron powder type Höganäs EO6O was employed per 100 parts by weight of silicone. The iron powder was surface-treated by phosphatization before being admixed to the silicone material. Then, the plug was molded in conventional manner. The detectability of the resulting plug corresponded to that of a metal sphere with a diameter of 2.5 mm.

For a glass down plug of the type described in our U.S. Pat. No. 4,614,487, where more detailed information on the design, production and so forth can be found, iron powder of the above type was loosely applied on top of the glass down piece before this was formed into a plug around a plunger and simultaneously was provided with an outer casing. After remaining treatment and handling of the plug, the iron powder was found to be freely distributed essentially throughout the plug. The amount of iron powder employed amounted to approximately three times the weight of the glass down.

In the present application, the term 'hearing-protector plug' is to be interpreted in a broad sense, thus including also a band or cord connected to the plug proper. If so, also the band or cord may, in accordance with the invention, be provided with the detectable means in the same way as the plug or plugs connected thereto. This considerably increases the detectability in banded or corded ear plugs.

I claim:

1. Hearing-protector plug adapted to be applied in the ear, comprising:

a plug material; and means for enabling tracing of said plug material with detection equipment operating magnetically, said means for enabling tracing comprising a powder distributed in said plug material, the particle size of the powder being up to about 300 µm.

2. Hearing-protector plug according to claim 1, wherein said means for enabling tracing is homogeneously distributed throughout the plug material.

3. Hearing-protector plug according to claim 1, wherein said means for enabling tracing comprises an integral part of said plug material.

4. Hearing-protector plug according to claim 1, wherein said powder has a particle size of between about 50 µm and 250 µm.

5. Hearing-protector plug according to claim 4, wherein said powder has a particle size of about 80 µm.

6. Hearing-protector plug according to claim 1, wherein said means for enabling tracing comprises iron powder.

7. Hearing-protector plug according to claim 1, wherein said plug material comprises a molded material, said means for enabling tracing being added to said plug material prior to molding.

8. Hearing-protector plug according to claim 7, wherein said plug material comprises a silicone material.

9. Hearing-protector plug according to claim 1, wherein said plug material comprises a foamed plastic, said means for enabling tracing being added prior to foaming.

10. Hearing-protector plug according to claim 8, comprising between about 10 to 50 parts by weight of iron powder per 100 parts by weight of silicone material.

11. Hearing-protector plug according to claim 1, wherein said powder comprises iron powder homogeneously distributed throughout said plug material.

12. Hearing-protector plug adapted to be applied to the ear, comprising:

a plug material comprising glass fibers; and means for enabling tracing of said plug material with detection equipment, said means for enabling tracing comprising a powder being distributed in said plug material in finely-divided particulate form.

13. Hearing-protector plug according to claim 12, wherein said means for enabling tracing is freely mixed with said glass fibers.

14. Hearing-protector plug according to claim 13, including an outer casing on said plug material.

15. Hearing-protector plug according to claim 12, wherein said means for enabling tracing is applied to said glass fibers by a finishing technique.

* * * * *

UNITED STATES PATENT AND TRADEMARK OFFICE
CERTIFICATE OF CORRECTION

PATENT NO. : 5,557,077
DATED : September 17, 1996
INVENTOR(S) : Bengt G. BERG

It is certified that error appears in the above-indentified patent and that said Letters Patent is hereby corrected as shown below:

On the cover, in section [22], "PCT Filed", change "Dec. 16, 1993" to ---Apr. 13, 1992---.

Signed and Sealed this

Twenty-fourth Day of June, 1997

Attest:

BRUCE LEHMAN

*Attesting Officer*        *Commissioner of Patents and Trademarks*